United States Patent
Kim et al.

(10) Patent No.: US 11,584,648 B2
(45) Date of Patent: Feb. 21, 2023

(54) METHOD FOR PREPARING OCTACALCIUM PHOSPHATE AND OCTACALCIUM PHOSPHATE PREPARED THEREBY

(71) Applicant: HUDENS BIO CO., LTD., Gwangju (KR)

(72) Inventors: Suk Young Kim, Gyeongsangbuk-do (KR); Joo Seong Kim, Gyeongsangbuk-do (KR)

(73) Assignee: HUDENS BIO CO., LTD., Gwangju (KR)

( * ) Notice: Subject to any disclaimer, the term of this patent is extended or adjusted under 35 U.S.C. 154(b) by 194 days.

(21) Appl. No.: 16/757,502

(22) PCT Filed: Oct. 19, 2018

(86) PCT No.: PCT/KR2018/012437
§ 371 (c)(1),
(2) Date: Apr. 20, 2020

(87) PCT Pub. No.: WO2019/078681
PCT Pub. Date: Apr. 25, 2019

(65) Prior Publication Data
US 2021/0188639 A1     Jun. 24, 2021

(30) Foreign Application Priority Data
Oct. 20, 2017    (KR) .................. 10-2017-0136721

(51) Int. Cl.
*C01B 25/32* (2006.01)
(52) U.S. Cl.
CPC ........ *C01B 25/327* (2013.01); *C01P 2002/60* (2013.01); *C01P 2002/72* (2013.01); *C01P 2004/03* (2013.01)

(58) Field of Classification Search
CPC ................................................... C01B 25/327
See application file for complete search history.

(56) References Cited

U.S. PATENT DOCUMENTS 4,335,086 A      6/1982 Spencer

FOREIGN PATENT DOCUMENTS

| EP | 0 383 568 A2 | 8/1990 |
|----|--------------|--------|
| JP | H05-221619 A | 8/1993 |

(Continued)

OTHER PUBLICATIONS

Office action dated Jul. 6, 2021 from Japan Intellectual Property Office in a counterpart Japanese Patent Application No. 2020-542517 (English translation is also submitted herewith.).

(Continued)

*Primary Examiner* — James A Fiorito
(74) *Attorney, Agent, or Firm* — The PL Law Group, PLLC (57) ABSTRACT

The present invention relates to a method of quickly preparing a large amount of octacalcium phosphate and octacalcium phosphate prepared thereby. A method of preparing octacalcium phosphate according to an embodiment of the present invention includes preparing a calcium phosphate solution, controlling an initial pH by controlling a pH of the calcium phosphate solution to a range from 5 to 6 using an acidic solution at a time point at which the pH of the calcium phosphate solution increases, heating the calcium phosphate solution to a temperature ranging from 60° C. to 90° C., and controlling a terminal pH by controlling the pH of the calcium phosphate solution to a range from 5 to 6 using a basic solution at a time point at which the pH of the heated calcium phosphate solution decreases.

7 Claims, 4 Drawing Sheets

(56) References Cited

FOREIGN PATENT DOCUMENTS

| | | |
|---|---|---|
| JP | H06-122510 A | 5/1994 |
| JP | 2005-097081 A | 4/2005 |
| JP | 2006-008429 A | 1/2006 |
| JP | 2008-222506 A | 9/2008 |
| JP | 4407416 B2 | 2/2010 |
| KR | 10-2004-0079190 A | 9/2004 |
| KR | 10-2007-0008328 A | 1/2007 |
| KR | 10-2010-0011395 A | 2/2010 |

OTHER PUBLICATIONS

European Search Report for EP18868693.5 dated Jun. 18, 2021 from European patent office in a counterpart European patent application.

Michele Freche et al., "Calcium Phosphate Precipitation in the 60-80° C. Range",Journal of Crystal Growth, Apr. 1, 1989, pp. 947-954, vol. 94, No. 4, Amsterdam,NL.

Fedotov, A. Yu et al., "Preparation of Octacalcium Phosphate from Calcium Carbonate Powder" Inorganic Materials, 2013, pp. 1148-1151, vol. 49, No. 11.

Selen Mandel, A. Cuneyt Tas , "Brushite ($CaHPO_4·2H_2O$) to octacalcium phosphate ($Ca_8(HPO_4)_2(PO_4)_4·5H_2O$) transformation in DMEM solutions at 36.5 ° C." Materials Science and Engineering C 30, 2010, pp. 245-254.

International Search Report for PCT/KR2018/012437 dated Jan. 31, 2019.

Office action dated May 18, 2020 from Korea Intellectual Property Office in a counterpart Korea Patent Application No. KR10-2018-0125451 (English translation is also submitted herewith.).

Example 1

Example 2

Comparative Example 1

Comparative Example 2

METHOD FOR PREPARING OCTACALCIUM PHOSPHATE AND OCTACALCIUM PHOSPHATE PREPARED THEREBY

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/012437, filed Oct. 19, 2018 which claims priority to the benefit of Korean Patent Application No. 10-2017-0136721 filed in the Korean Intellectual Property Office on Oct. 20, 2017, the entire contents of which are incorporated herein by reference.

TECHNICAL FIELD

The present invention relates to a method of preparing octacalcium phosphate and octacalcium phosphate prepared using the same.

BACKGROUND ART

Hydroxyapatite (HA) is mainly found in the teeth and bones in the body. Therefore, HA is mainly used to improve the proliferation of bone cells or as a coating agent to promote the ingrowth of bones in the field of fillers or artificial implants to replace broken bones. However, HA is problematic because reabsorption into the body does not occur well, even after bone regeneration in the broken region.

Hence, research is ongoing into increasing the reabsorption rate in the body and biocompatibility for bone cells using octacalcium phosphate (OCP), which is a precursor of HA.

However, conventional methods of synthesizing OCP have problems such as difficulties in obtaining highly pure OCP, high production costs and low yield. Therefore, there remains the need for research on an optimal OCP synthesis (preparation) method in order to solve the above problems.

SUMMARY

The present invention is intended to provide a method of quickly preparing a large amount of octacalcium phosphate and octacalcium phosphate prepared using the same.

The objectives of the present invention are not limited to the foregoing, and it is to be understood that other objectives not mentioned herein will be readily anticipated by those skilled in the art from the following description.

An aspect of the present invention provides a method of preparing octacalcium phosphate, including preparing a calcium phosphate solution, controlling an initial pH by controlling the pH of the calcium phosphate solution to a range from 5 to 6 using an acidic solution at the time point at which the pH of the calcium phosphate solution increases, heating the calcium phosphate solution to a temperature ranging from 60° C. to 90° C., and controlling a terminal pH by controlling the pH of the calcium phosphate solution to a range from 5 to 6 using a basic solution at the time point at which the pH of the heated calcium phosphate solution decreases.

In addition, another aspect of the present invention provides octacalcium phosphate prepared using the above method.

According to an embodiment of the present invention, a method of preparing octacalcium phosphate is capable of providing highly pure octacalcium phosphate.

According to an embodiment of the present invention, the method of preparing octacalcium phosphate is capable of preparing octacalcium phosphate within a short time.

According to an embodiment of the present invention, the method of preparing octacalcium phosphate is capable of ensuring process profitability by reducing production costs.

According to an embodiment of the present invention, the method of preparing octacalcium phosphate is capable of obtaining octacalcium phosphate at high yield.

DETAILED DESCRIPTION

As used throughout this specification, when any part is said to "comprise" or "include" any element, this means that other elements are not necessarily excluded, but may be further included unless otherwise stated.

As used throughout this specification, the term "step to" or "step of" does not mean "step for".

The present inventors have made great efforts to solve problems, such as low purity and low yield, encountered in existing octacalcium phosphate synthesis methods, including, for example, separately mixing a calcium-containing powder and a phosphorus-containing powder in a cell culture medium to afford octacalcium phosphate, and have devised the following.

Specifically, the present inventors have devised a method of preparing octacalcium phosphate using a calcium phosphate solution containing both phosphorus and calcium in an aqueous solvent, rather than the cell culture medium. The method of preparing octacalcium phosphate according to the present invention is capable of obtaining highly pure octacalcium phosphate, and is advantageous because of the short preparation time, reduced preparation costs, and increased octacalcium phosphate yield.

Hereinafter, a detailed description will be given of the present specification.

An aspect of the present invention pertains to a method of preparing octacalcium phosphate including preparing a calcium phosphate solution, controlling an initial pH by controlling the pH of the calcium phosphate solution to a range from 5 to 6 using an acidic solution at the time point at which the pH of the calcium phosphate solution increases, heating the calcium phosphate solution to a temperature ranging from 60° C. to 90° C., and controlling a terminal pH by controlling the pH of the calcium phosphate solution to a range from 5 to 6 using a basic solution at the time point at which the pH of the heated calcium phosphate solution decreases.

Individual steps of the preparation method of the present invention are specified below.

Preparing Calcium Phosphate Solution

Figure 1:
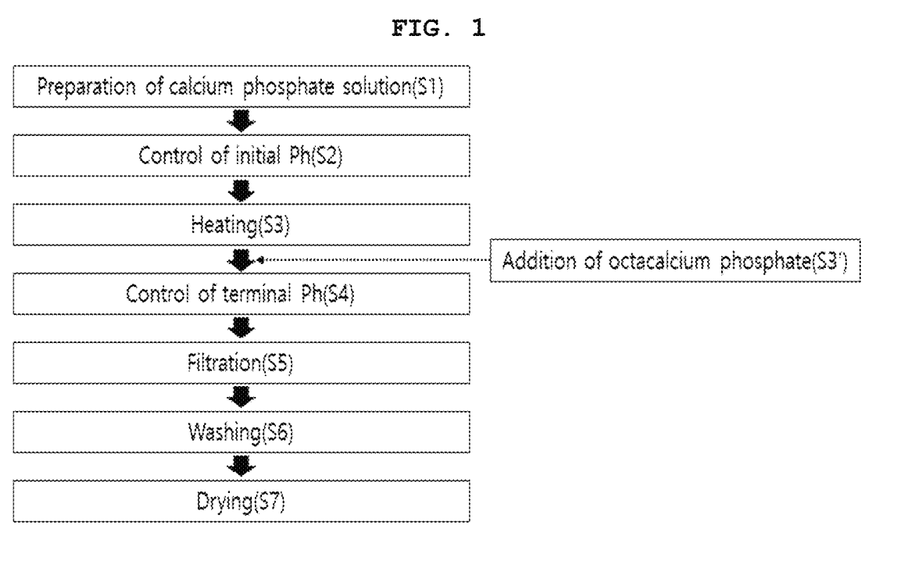
FIG. 1 is a flowchart showing a process of preparing octacalcium phosphate according to an embodiment of the present invention.

In an embodiment of the present invention, the method of preparing octacalcium phosphate includes preparing a calcium phosphate solution. As shown in FIG. 1, preparing the calcium phosphate solution may correspond to (S1) of FIG. 1.

In an embodiment of the present invention, preparing the calcium phosphate solution includes mixing a calcium phosphate hydrate and a solvent, and the amount of the calcium phosphate hydrate may be less than 10 g but exceeding 1 g relative to 1 ℓ of the solvent. Specifically, the amount of the calcium phosphate hydrate may range from 3 g to less than 10 g, from greater than 1 g to 8 g, from 3 g to 8 g, from 3 g to 6 g, from 4 g to 8 g, or from 4 g to 6 g, relative to 1 ℓ of the solvent, and is preferably 5 g.

When the amount of the calcium phosphate hydrate is adjusted within the above range, octacalcium phosphate may be obtained at a constant precipitation rate, and the amount of octacalcium phosphate that is produced may be maximized. Specifically, when the amount of the calcium phosphate hydrate falls in the above range, the amount of precipitation or production of octacalcium phosphate, specifically mineral octacalcium phosphate, may be increased.

As used herein, the term "precipitation" may mean production of a solid material in a liquid.

In an embodiment of the present invention, the calcium phosphate hydrate may include dicalcium phosphate dihydrate (DCPD). Specifically, the dicalcium phosphate dihydrate is a precursor of octacalcium phosphate, and octacalcium phosphate may be precipitated from the dicalcium phosphate dihydrate contained in the calcium phosphate solution. The octacalcium phosphate may be a solid-state crystal produced in the calcium phosphate solution.

In an embodiment of the present invention, the density of the calcium phosphate hydrate may range from 2 g/cm$^3$ to 2.5 g/cm$^3$, and may be particularly 2.32 g/cm$^3$. Moreover, the calcium phosphate hydrate may have a monoclinic crystal system, and the octacalcium phosphate to be produced may have a triclinic crystal system.

In an embodiment of the present invention, the molar ratio of calcium (Ca) and phosphorus (P) in the calcium phosphate hydrate may be 1:0.75 to 1:1.1.

In an embodiment of the present invention, the solvent may be an aqueous solvent, particularly water or a mixed solvent of water and an alcoholic solvent, and more particularly water. Moreover, the solvent may be distilled water or deionized water. Also, the solvent may be a neutral solvent, and particularly, the pH of the solvent may be about 7.

As the solvent, a cell culture medium such as DMEM (Dulbecco's Modified Eagle Medium), etc. is conventionally used, but it is expensive, and moreover, when octacalcium phosphate is prepared using the same, the yield thereof is low.

On the other hand, the method of preparing octacalcium phosphate according to an embodiment of the present invention uses an aqueous solvent, preferably distilled water or deionized water, as the solvent, and thus octacalcium phosphate may be prepared at relatively low cost and high yield compared to when using the conventional method.

In an embodiment of the present invention, the calcium phosphate solution may be a suspension solution in which calcium phosphate hydrate powder or particles are dispersed in the solvent. Moreover, the calcium phosphate solution may be a suspension solution in which calcium phosphate hydrate powder or heterogeneous seed particles are dispersed in the solvent.

In an embodiment of the present invention, the calcium phosphate solution may be prepared by mixing a calcium salt solution and a phosphate solution. The calcium salt of the calcium salt solution may include at least one selected from among calcium citrate, calcium gluconate, calcium glycerophosphate, calcium oxide, calcium hydroxide, calcium chloride, calcium lactate, calcium phosphate tribasic, calcium phosphate dibasic, calcium phosphate monobasic, calcium carbonate and calcium sulfate, but the kind of calcium salt is not limited.

Also, the phosphate of the phosphate solution may include at least one selected from among $(NH_4)_2HPO_4$ and $(NH_4)H_2PO_4$, but the kind of phosphate is not limited.

Furthermore, the calcium salt solution and the phosphate solution may include an aqueous solvent. The aqueous solvent contained in the calcium salt solution and the phosphate solution may be the same as the solvent that is mixed with the calcium phosphate hydrate described above.

Controlling Initial pH

In an embodiment of the present invention, the method of preparing octacalcium phosphate includes controlling an initial pH by controlling the pH of the calcium phosphate solution to a range from 5 to 6 using an acidic solution at the time point at which the pH of the calcium phosphate solution increases. As shown in FIG. 1, controlling the initial pH may correspond to (S2) of FIG. 1.

In an embodiment of the present invention, when controlling the initial pH, the pH of the calcium phosphate solution may be controlled to the range from 5 to 6, from 5 to 5.5, or from 5 to 5.2.

Specifically, controlling the pH may be performed in a manner in which, during the preparation of the calcium phosphate solution by mixing the solvent and the calcium phosphate hydrate or during the preparation of the calcium phosphate solution by mixing the calcium salt solution and the phosphate solution, the pH of the calcium phosphate solution may be controlled to the above range using the acidic solution at the time point at which the pH of the calcium phosphate solution increases.

In an embodiment of the present invention, the pH of the calcium phosphate solution is controlled to the above range when controlling the initial pH, whereby octacalcium phosphate may be obtained at a high precipitation rate. Specifically, if the pH of the calcium phosphate solution falls out of the above range, octacalcium phosphate may not be sufficiently prepared even when subsequent steps of heating the calcium phosphate solution and maintaining the pH thereof in an appropriate range are performed. Moreover, when controlling the initial pH, the pH of the calcium phosphate solution is maintained in the above range, thereby preventing the formation of hydroxyapatite (HA) and preparing octacalcium phosphate at a high precipitation rate in the subsequent step of controlling the terminal pH.

In an embodiment of the present invention, controlling the initial pH may include mixing the calcium phosphate hydrate and the solvent or mixing the calcium salt solution and the phosphate solution, followed by adding the acidic solution thereto.

Specifically, when the calcium phosphate hydrate and the solvent are mixed, the pH of the calcium phosphate solution may increase due to the basic calcium phosphate hydrate. Alternatively, when the calcium salt solution and the phosphate solution are mixed, for example, the calcium salt, $Ca(CH_3COO)_2$, may increase the number of $OH^-$ ions in the aqueous solution, thus raising the pH of the calcium phosphate solution.

The octacalcium phosphate may be effectively prepared by controlling the pH of the calcium phosphate solution to the above range by adding the acidic solution at the time point at which the pH of the calcium phosphate solution increases.

In an embodiment of the present invention, the concentration of the acidic solution may range from 1 mol/L to 3 mol/L or may be 2 mol/L. Moreover, the acidic solution may be an acetic acid aqueous solution, a hydrochloric acid aqueous solution, etc., but the kind thereof is not limited.

Heating Calcium Phosphate Solution

In an embodiment of the present invention, the method of preparing octacalcium phosphate includes heating the calcium phosphate solution to a temperature ranging from 60° C. to 90° C. As shown in FIG. 1, heating the calcium phosphate solution may correspond to (S3) of FIG. 1.

Particularly, heating the calcium phosphate solution may include heating the calcium phosphate solution with stirring, and more particularly heating the calcium phosphate solution on a hot plate with stirring.

In an embodiment of the present invention, when heating the calcium phosphate solution, the calcium phosphate solution may be heated to a temperature ranging from 65° C. to 90° C., from 60° C. to 85° C., from 65° C. to 85° C., from 65° C. to 80° C., from 70° C. to 85° C., or from 70° C. to 80° C. When the calcium phosphate solution is heated to the above temperature range, evaporation of the solvent of the calcium phosphate solution may be prevented, thus preventing a deterioration in the stability of the calcium phosphate solution due to evaporation of the solvent. Moreover, when the temperature of the calcium phosphate solution falls in the above range, octacalcium phosphate may be quickly precipitated from the calcium phosphate solution and the amount of octacalcium phosphate that is produced may be increased.

Also, when the calcium phosphate solution is heated to the above temperature range, the extent of ionization of the calcium phosphate hydrate may be improved, thus preventing a problem in which the reaction for producing octacalcium phosphate is not induced due to reduced ionization of the calcium phosphate hydrate for a given amount of the calcium phosphate solution.

In an embodiment of the present invention, elevating the temperature of the calcium phosphate solution may include heating the calcium phosphate solution on a mantle with stirring or heating the calcium phosphate solution on a hot plate with stirring, but the process of heating the calcium phosphate solution is not limited.

In an embodiment of the present invention, heating the calcium phosphate solution may include heating the calcium phosphate solution from room temperature to a temperature ranging from 65° C. to 90° C., from 60° C. to 85° C., from 65° C. to 85° C., from 65° C. to 80° C., from 70° C. to 85° C., or from 70° C. to 80° C.

When the calcium phosphate solution is heated from room temperature to the above temperature range, the ionization process may be carried out to produce octacalcium phosphate from the calcium phosphate hydrate, and high energy efficiency may be achieved. Specifically, when the calcium phosphate solution is heated from room temperature to the above temperature range, the ionization process in which octacalcium phosphate is formed from calcium phosphate hydrate may be prevented from progressing differently, and moreover, it is possible to prevent a reduction in efficiency in terms of energy and economy due to the long time required for heating.

As used herein, room temperature may indicate a temperature at any one point among temperatures of 20° C. to 30° C., and may particularly indicate 25° C.

Adding Heterogeneous Seed

In an embodiment of the present invention, the method of preparing octacalcium phosphate may further include adding a heterogeneous seed to the heated calcium phosphate solution before controlling the terminal pH. As shown in FIG. 1, adding the heterogeneous seed may correspond to (S3') of FIG. 1.

In an embodiment of the present invention, when the heated calcium phosphate solution is added with the heterogeneous seed, octacalcium phosphate may be quickly precipitated from the calcium phosphate solution, and the amount of octacalcium phosphate that is precipitated may be effectively increased. The heterogeneous seed may include at least one selected from among octacalcium phosphate and dicalcium phosphate dihydrate.

In an embodiment of the present invention, the heterogeneous seed that is added to the heated calcium phosphate solution may function as a crystal seed. When the calcium phosphate solution is added with the heterogeneous seed, octacalcium phosphate crystal may be grown at a fast rate around the heterogeneous seed, namely the crystal seed, and the amount of octacalcium phosphate that is produced may be stably increased.

In an embodiment of the present invention, the average particle size of the heterogeneous seed that is added to the calcium phosphate solution may range from 1 nm to 1 μm. Particularly, the average particle size of the heterogeneous seed that is added to the calcium phosphate solution may range from 5 nm to 900 nm, from 10 nm to 750 nm, from 50 nm to 600 nm, from 100 nm to 500 nm, or from 200 nm to 350 nm. When the heterogeneous seed having the average particle size in the above range is added to the calcium phosphate solution, octacalcium phosphate may be quickly precipitated from the calcium phosphate solution, and the amount of octacalcium phosphate that is precipitated may be effectively increased.

A process of measuring the average particle size of a powder may be adopted without limitation in the art in order to measure the average particle size of the heterogeneous seed that is added to the calcium phosphate solution. For example, the average particle size may be measured through filtration of the heterogeneous seed using a sieve having different hole sizes.

In an embodiment of the present invention, the amount of the heterogeneous seed that is added to the calcium phosphate solution may range from 0.01 parts by weight to 0.5 parts by weight based on 100 parts by weight of the calcium phosphate solution. Particularly, the amount thereof may range from 0.05 parts by weight to 0.45 parts by weight, from 0.07 parts by weight to 0.3 parts by weight, from 0.1 parts by weight to 0.2 parts by weight, or from 0.25 parts by weight to 0.45 parts by weight, based on 100 parts by weight of the calcium phosphate solution. When the amount of the heterogeneous seed that is added to the calcium phosphate solution is adjusted within the above range, octacalcium phosphate may be quickly precipitated from the calcium phosphate solution, and the amount of octacalcium phosphate that is precipitated may be effectively increased.

Controlling Terminal pH

In an embodiment of the present invention, the method of preparing octacalcium phosphate includes controlling a terminal pH by controlling the pH of the calcium phosphate solution to a range from 5 to 6 using a basic solution at the time point at which the pH of the heated calcium phosphate solution decreases. As shown in FIG. 1, controlling the terminal pH may correspond to (S4) of FIG. 1.

In an embodiment of the present invention, controlling the terminal pH may include controlling the pH of the heated calcium phosphate solution to a range from 5 to 6, from 5 to 5.5, or from 5 to 5.2.

Specifically, controlling the terminal pH may be performed in a manner in which, while stirring the heated calcium phosphate solution, the pH of the calcium phosphate solution is controlled to the above range using a basic solution at the time point at which the pH of the heated calcium phosphate solution decreases.

When the pH of the heated calcium phosphate solution is controlled to the above range, octacalcium phosphate may be quickly precipitated from the calcium phosphate solution. Moreover, when the pH of the heated calcium phosphate solution falls in the above range, the amount of octacalcium phosphate that is precipitated may be effectively increased.

In an embodiment of the present invention, controlling the terminal pH may be performed by adding a basic solution at the time point at which the pH of the calcium phosphate solution decreases.

In an embodiment of the present invention, the pH of the calcium phosphate solution is lowered to less than 5 while acidic octacalcium phosphate is produced in the calcium phosphate solution. As such, when the basic solution is added in an appropriate amount, the pH of the calcium phosphate solution may be controlled and maintained in the above range.

In an embodiment of the present invention, the basic solution may be ammonia water, but the kind thereof is not limited.

In an embodiment of the present invention, controlling the terminal pH may be performed while the temperature of the calcium phosphate solution is maintained in the range from 60° C. to 90° C., particularly from 65° C. to 90° C., from 60° C. to 85° C., from 65° C. to 85° C., from 65° C. to 80° C., from 70° C. to 85° C., or from 70° C. to 80° C.

In an embodiment of the present invention, when controlling the terminal pH, octacalcium phosphate may be produced at a rate ranging from 0.5 g/ℓ ·min to 1.5 g/ℓ ·min or at a rate of about 1 g/ℓ ·min. When octacalcium phosphate is produced at the above production rate, octacalcium phosphate may be produced in a shorter time than in the conventional octacalcium phosphate preparation process.

In an embodiment of the present invention, the precipitation efficiency of octacalcium phosphate from the calcium phosphate hydrate may be 85% or more, and preferably 99% or more.

As used herein, the term "precipitation efficiency" may mean the weight of the precipitated octacalcium phosphate crystal relative to the weight of the added octacalcium phosphate precursor, expressed as a percentage. Specifically, it may mean the weight of the precipitated octacalcium phosphate crystal relative to the weight of calcium phosphate hydrate or the total weight of calcium salt solution and phosphate solution, expressed as a percentage.

In an embodiment of the present invention, the method of preparing octacalcium phosphate may further include filtering the calcium phosphate solution having the controlled pH. As shown in FIG. 1, the filtration process may correspond to (S5) of FIG. 1.

In an embodiment of the present invention, filtering the calcium phosphate solution having the controlled pH may be performed by filtering the calcium phosphate solution having the controlled pH when controlling the initial pH and/or the calcium phosphate solution having the controlled pH when controlling the terminal pH.

In an embodiment of the present invention, filtering the calcium phosphate solution having the controlled pH may be performed using filter paper, and particularly, may be conducted by passing the calcium phosphate solution having the controlled pH through filter paper.

In an embodiment of the present invention, residue formed on the filter paper resulting from filtering the calcium phosphate solution having the controlled pH may include the octacalcium phosphate crystal precipitated from the calcium phosphate solution.

In an embodiment of the present invention, the method of preparing octacalcium phosphate may further include washing the residue of the filtered calcium phosphate solution. As shown in FIG. 1, the washing process may correspond to (S6) of FIG. 1.

Specifically, washing the residue may include washing the residue using a solvent, but the process thereof is not particularly limited. Moreover, the description of the solvent is as described above. By washing the residue, impurities other than the octacalcium phosphate crystal contained in the residue may be removed.

In an embodiment of the present invention, the method of preparing octacalcium phosphate may further include drying the washed residue. As shown in FIG. 1, the drying process may correspond to (S7) of FIG. 1.

In an embodiment of the present invention, drying the washed residue may be performed using a dryer. Moreover, the kind of dryer is not particularly limited, and the dryer may be appropriately selected from among dryers typically known in the art.

In an embodiment of the present invention, drying the washed residue may be performed at a temperature ranging from 70° C. to 90° C., and preferably a temperature of 80° C., for about 24 hr. Here, the drying temperature and the drying time are not particularly limited, and may be appropriately adjusted depending on the amount of the residue.

In an embodiment of the present invention, the washed residue is dried, thereby obtaining a highly pure octacalcium phosphate crystal.

Another aspect of the present invention pertains to octacalcium phosphate prepared using the above method.

In an embodiment of the present invention, the octacalcium phosphate thus prepared includes a first crystal, having a length ranging from 10 μm to 15 μm and a width ranging from 2 μm to 3 μm, and a second crystal, having a length ranging from 1 μm to 10 μm and a width ranging from 0.5 μm to 3 μm. Unlike conventionally known research results, in an embodiment of the present invention, octacalcium phosphate crystals having non-uniform sizes may be obtained, and crystals having two sizes may be obtained. A mixture of relatively small octacalcium phosphate crystal and relatively large octacalcium phosphate crystal may be prepared, and the mixture thus prepared may be mechanically crushed, whereby the size of the octacalcium phosphate crystal may be adjusted to a desired size. Moreover, since octacalcium phosphate crystal obtained through a conventional method has a uniform size, small crystals and large crystals contained in octacalcium phosphate according to an embodiment of the present invention may be easily distinguished in SEM images.

In an embodiment of the present invention, octacalcium phosphate, prepared by the above method and having precipitation efficiency of 85% or more, and preferably 99% or more, of octacalcium phosphate from the calcium phosphate hydrate, is provided.

In an embodiment of the present invention, the octacalcium phosphate may exhibit a peak corresponding to JCPDS No. 74-1301 based on the results of X-ray diffraction (XRD).

A better understanding of the present invention may be obtained via the following examples, which are set forth to illustrate the present invention. However, these examples may be modified into a variety of different forms, and are not to be construed as limiting the scope of the present invention. The examples of the present invention are provided to more fully explain the present specification to those having ordinary knowledge in the art to which the present invention pertains.

Example 1

A calcium phosphate solution was prepared by adding 1 ℓ of distilled water having a pH of 7 with 5 g of dicalcium phosphate dihydrate (DCPD, $CaHPO_4.2H_2O$). Here, the calcium phosphate solution was added with a 2 mol/L acetic acid standard solution so that the pH of the calcium phosphate solution was maintained at about 5. The temperature of the calcium phosphate solution was 25° C.

Thereafter, the calcium phosphate solution having the controlled pH was heated to 80° C. on a hot plate with stirring at 200 rpm. Thereafter, the heated calcium phosphate solution was added with, as a heterogeneous seed, an octacalcium phosphate powder having an average particle size of about 500 nm in an amount of 0.5 parts by weight based on 100 parts by weight of the calcium phosphate solution.

Thereafter, ammonia water was added whenever the pH of the calcium phosphate solution decreased, whereby the pH of the calcium phosphate solution was controlled to about 5, and this state was maintained for 5 min.

After 5 min, the calcium phosphate solution was filtered using filter paper (available from Whatman), and residue remaining on the filter paper was washed with 50 ml of ethanol, after which the washed residue was placed in a dryer and dried at 80° C. for 24 hr, thereby yielding octacalcium phosphate.

Example 2

A calcium phosphate solution was prepared by adding 1 ℓ of distilled water having a pH of 7 with 5 g of dicalcium phosphate dihydrate (DCPD, $CaHPO_4.2H_2O$). Here, the calcium phosphate solution was added with a 2 mol/L acetic acid standard solution so that the pH of the calcium phosphate solution was maintained at about 6. The temperature of the calcium phosphate solution was 25° C.

Thereafter, the calcium phosphate solution having the controlled pH was heated to 80° C. on a hot plate with stirring at 200 rpm. Thereafter, ammonia water was added whenever the pH of the calcium phosphate solution decreased, whereby the pH of the calcium phosphate solution was controlled to about 6, and this state was maintained for 5 min.

After 5 min, the calcium phosphate solution was filtered using filter paper (available from Whatman), and residue remaining on the filter paper was washed with 50 ml of ethanol, after which the washed residue was placed in a dryer and dried at 80° C. for 24 hr, thereby yielding octacalcium phosphate.

Comparative Example 1

This example was performed in the same manner as in Example 2, with the exception that the pH of the calcium phosphate solution was maintained at 7, but octacalcium phosphate was not detected.

Comparative Example 2

Octacalcium phosphate was obtained in the same manner as in Example 2, with the exception that the pH of the calcium phosphate solution was not controlled.

<Test Example and Evaluation>

1. Change in pH of Solution Over Time

Figure 2:
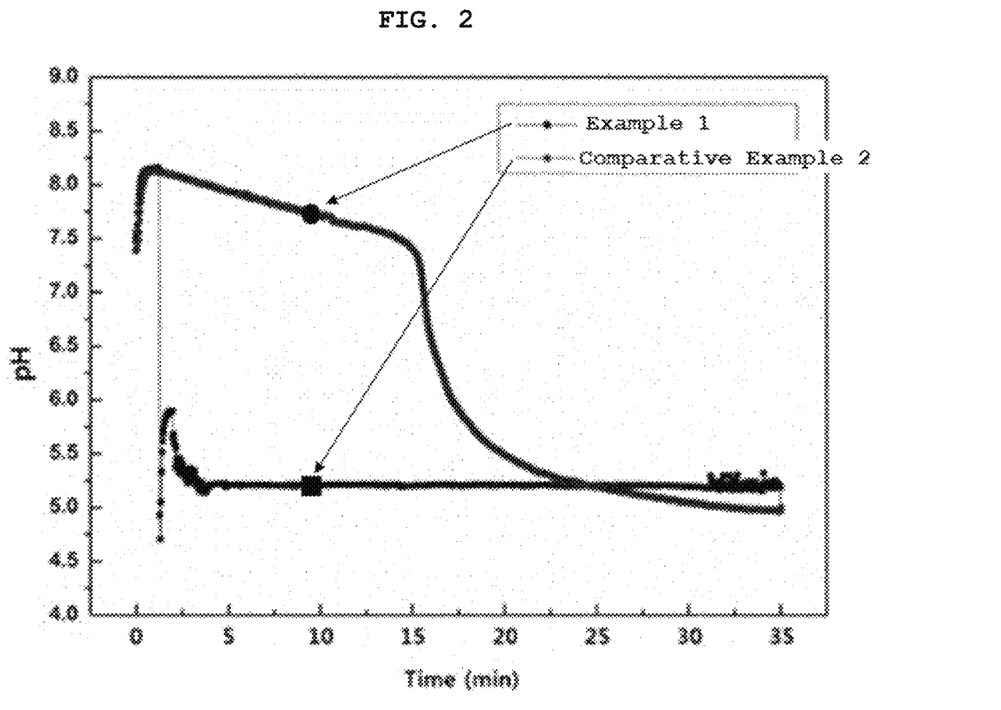
FIG. 2 shows changes in pH over time of Example 1 (controlled pH) and Comparative Example 2 (uncontrolled pH)

Changes in the pH of the solution over time during the preparation of Example 1 and Comparative Example 2 are shown in FIG. 2.

As shown in FIG. 2, in Comparative Example 2, in which distilled water was added with DCPD and then an additional acidic solution was not added thereto, the pH rapidly increased to 7 or more, gradually decreased up to about 15 min, and then drastically decreased after about 15 min. Moreover, after about 25 min, the pH of Comparative Example 2 was about 5, and the pH was slightly lowered thereafter.

Based on the results thereof in combination with the following conversion measurement results, when the temperature and the pH of the calcium phosphate solution fell in the ranges according to the embodiment of the present invention, octacalcium phosphate precipitate was observed, but when the initial pH and the terminal pH were not controlled, OCP could not be obtained at high conversion efficiency from DCPD.

As shown in FIG. 2, in Example 1, in which the pH was maintained at about 5 by adding the acidic solution immediately after distilled water was added with DCPD, there was a sudden change in pH after about 30 min, and the pH was maintained at about 5 by the addition of the basic solution at the same time therewith.

Specifically, octacalcium phosphate was prepared under conditions of temperature and initial pH and terminal pH according to the embodiment of the present invention, and the initial pH and the terminal pH were maintained in the above pH ranges using the acidic solution and the basic solution, respectively, from which the conversion efficiency of octacalcium phosphate was estimated to increase.

2. X-Ray Diffraction Analysis

The kinds and relative amounts of components contained in Example 1 (pH 5), Example 2 (pH 6), Comparative Example 1 (pH 7) and Comparative Example 2 (uncontrolled) were measured using an X-ray diffractometer (X'Pert HighScore Plus, available from PANalytical). The results thereof are shown in FIG. 3.

Figure 3:
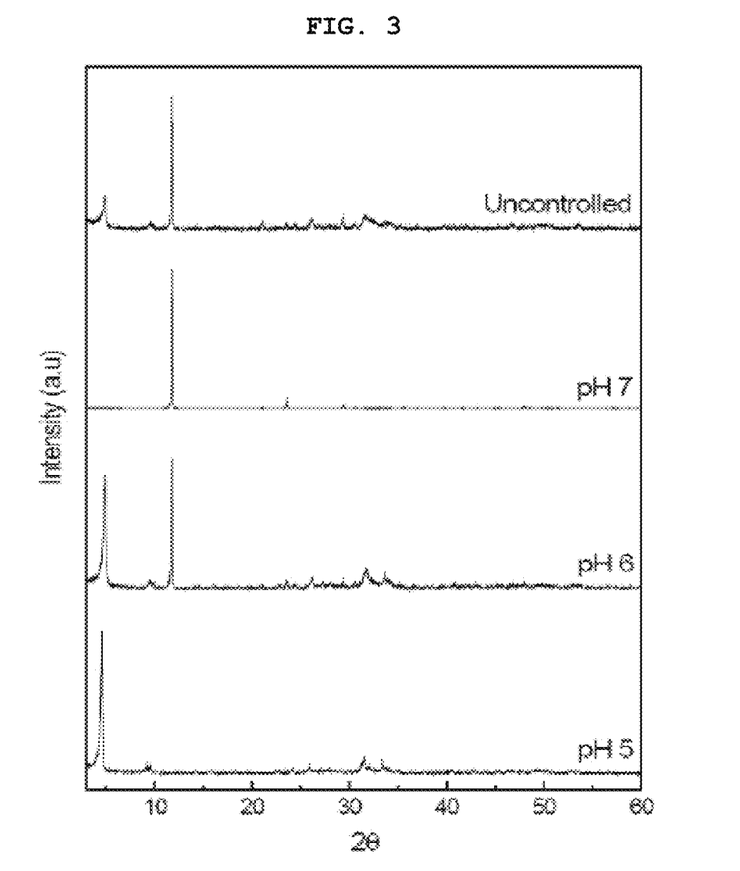
FIG. 3 shows the results of X-ray diffraction (XRD) of Example 1, Example 2, Comparative Example 1 and Comparative Example 2.

As shown in FIG. 3, Example 1 exhibited a peak of JCPDS No. 74-1301 corresponding to octacalcium phosphate.

As shown in FIG. 3, Example 2 exhibited a peak of JCPDS No. 72-1243, corresponding to hydroxyapatite, as well as the peak of JCPDS No. 74-1301.

Also, as shown in FIG. 3, Comparative Example 1 exhibited a peak of JCPDS No. 09-0077 corresponding to DCPD, and the peak of JCPDS No. 72-1243.

Also, as shown in FIG. 3, Comparative Example 2 exhibited all of the peak of JCPDS No. 74-1301, the peak of JCPDS No. 09-0077 and the peak of JCPDS No. 72-1243.

Based on the results of FIG. 3, it was possible to precipitate a large amount of OCP in Example 1 and Example 2, but in Comparative Example 1 and Comparative Example 2, in which the controlled pH fell out of the range according to the embodiment of the present invention or the pH was not controlled, OCP was precipitated in a very small amount or was not precipitated.

3. Measurement of OCP Precipitation Efficiency

Figure 4:
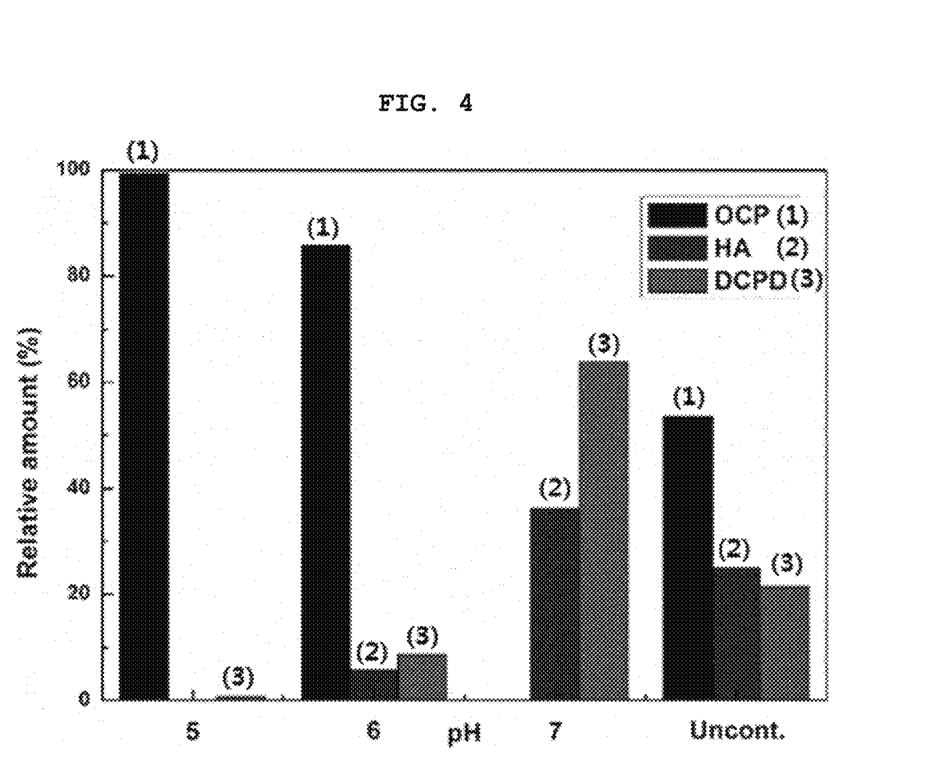
FIG. 4 shows the relative amount of each component in Example 1, Example 2, Comparative Example 1 and Comparative Example 2.

After the X-ray diffraction analysis, using the Rietveld function of the X-ray diffractometer, the relative amounts of DCPD, OCP and hydroxyapatite (HA) contained in Example 1 (pH 5), Example 2 (pH 6), Comparative Example 1 (pH 7) and Comparative Example 2 (uncontrolled pH) were measured. The results thereof are shown in Table 1 below and in FIG. 4.

TABLE 1

|  | OCP (%) | HA (%) | DCPD (%) | Total |
|---|---|---|---|---|
| Example 1 | 99.3 | 0.0 | 0.7 | 100 |
| Example 2 | 85.7 | 5.6 | 8.7 | 100 |
| Comparative Example 1 | 0.0 | 36.2 | 63.8 | 100 |
| Comparative Example 2 | 53.5 | 25.0 | 21.5 | 100 |

As is apparent from Table 1, in Example 1 and Example 2, in which the pH of the solution before and after the production of octacalcium phosphate were maintained at 5 and 6, respectively, DCPD was mostly consumed, and a high OCP precipitation efficiency of 85% or more was obtained.

However, in Comparative Example 1, in which the pH of the solution was maintained at 7, HA was immediately generated, and in Comparative Example 2, in which the pH was not controlled, OCP was prepared at a low precipitation efficiency of 60% or less.

4. Scanning Electron Microscopy

Example 1, Example 2, Comparative Example 1 and Comparative Example 2 were observed using a scanning electron microscope (SEM). The images thereof are shown in FIG. 5.

Figure 5:
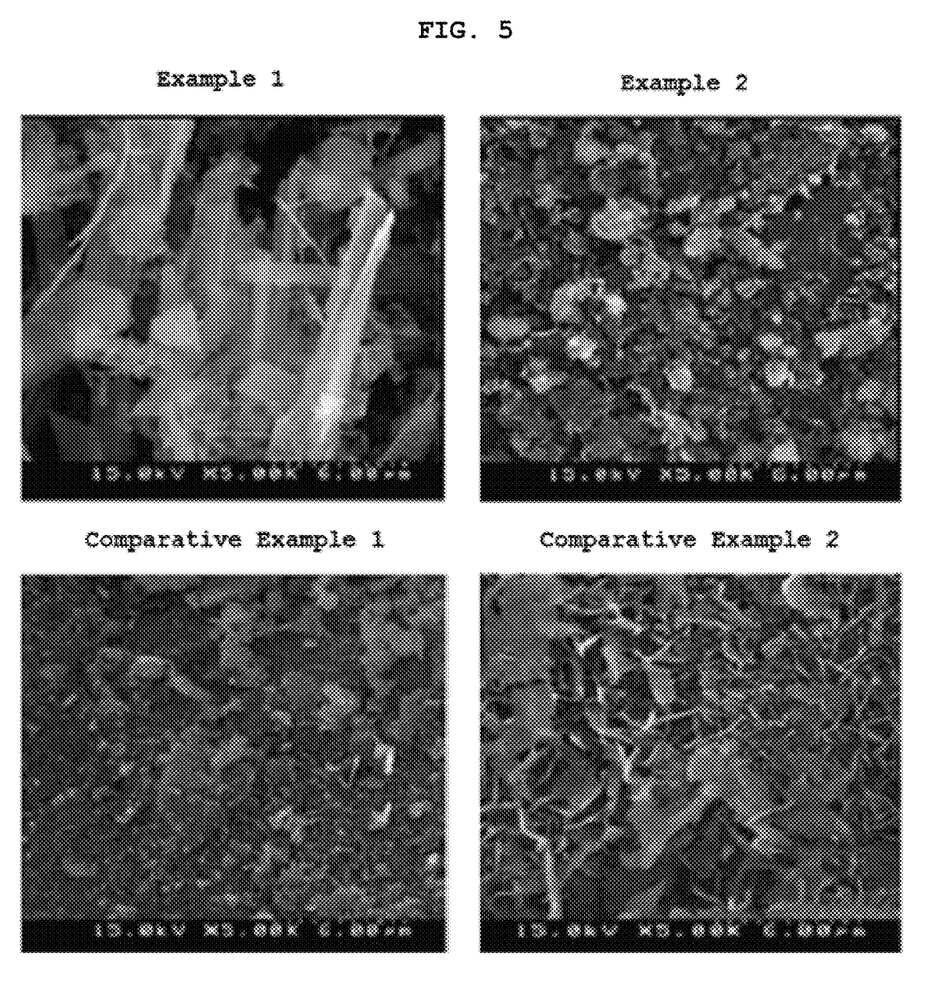
FIG. 5 shows scanning electron microscope (SEM) images of Example 1, Example 2, Comparative Example 1 and Comparative Example 2.

As shown in FIG. 5, in the SEM cross-sectional images, a relatively small plate-like material corresponding to OCP was observed, and the OCP was detected in a larger amount in Example 1 and Example 2 than in Comparative Example 1 and Comparative Example 2.

Based on the above test results, in order to increase the production yield of octacalcium phosphate, it can be confirmed that the initial pH of the calcium phosphate solution has to be maintained in the range according to the embodiment of the present invention, the initial temperature of the solution has to be elevated to the range according to the embodiment of the present invention, and then the pH of the calcium phosphate solution has to be maintained in the range according to the embodiment of the present invention.

Moreover, with reference to FIG. 5, it was confirmed for octacalcium phosphate prepared through a conventional method that a ribbon-type octacalcium phosphate crystal having a uniform size was formed, and it was confirmed for octacalcium phosphate of Example 1, prepared by adding the heated calcium phosphate solution with the heterogeneous seed, that two kinds of ribbon-type crystals having different sizes were included. Specifically, the octacalcium phosphate prepared in Example 1 was confirmed to include a first crystal having a length ranging from 10 µm to 15 µm and a width ranging from 2 µm to 3 µm, and a second crystal having a length ranging from 1 µm to 10 µm and a width ranging from 0.5 µm to 3 µm.

The invention claimed is:

1. A method of preparing octacalcium phosphate, comprising:
    preparing a calcium phosphate solution;
    controlling an initial pH by controlling a pH of the calcium phosphate solution to a range from 5 to 6 using an acidic solution;
    heating the calcium phosphate solution of which the initial pH is controlled to a temperature ranging from 60° C. to 90° C.;
    adding a heterogeneous seed comprising at least one selected from among octacalcium phosphate and dicalcium phosphate dihydrate to the heated calcium phosphate solution;
    after adding the heterogeneous seed, adjusting a terminal pH by controlling the pH of the heated calcium phosphate solution to which the heterogeneous seed is added to a range from 5 to 6.

2. The method of claim 1, wherein the preparing of the calcium phosphate solution comprises mixing a calcium phosphate hydrate and a solvent; and
    an amount of the calcium phosphate hydrate being less than 10 g but exceeding 1 g relative to 1 ℓ of the solvent.

3. The method of claim 2, wherein the calcium phosphate hydrate comprises dicalcium phosphate dihydrate.

4. The method of claim 1, wherein an average particle size of the heterogeneous seed that is added to the calcium phosphate solution ranges from 1 nm to 1 µm.

5. The method of claim 1, wherein an amount of the heterogeneous seed that is added to the calcium phosphate solution ranges from 0.01 parts by weight to 0.5 parts by weight based on 100 parts by weight of the calcium phosphate solution.

6. The method of claim 1, wherein the controlling the terminal pH is performed while a temperature of the heated calcium phosphate solution is maintained in a range from 60° C. to 90° C.

7. The method of claim 1, wherein, in the controlling the terminal pH, the octacalcium phosphate is produced at a rate ranging from 0.5 g/ℓ ·min to 1.5 g/ℓ ·min.

* * * * *